(12) United States Patent
Nettelhoff et al.

(10) Patent No.: US 6,450,681 B1
(45) Date of Patent: Sep. 17, 2002

(54) PROCESS FOR DISSOLVING ALBUMIN FLAKES IN A LIQUID AND ARRANGEMENT FOR CARRYING OUT THE PROCESS

(75) Inventors: Hubert Nettelhoff; Jürgen Römisch, both of Marburg (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/461,242

(22) Filed: Dec. 16, 1999

(30) Foreign Application Priority Data

Dec. 17, 1998 (DE) .......................................... 198 58 188

(51) Int. Cl.⁷ .................................................. B01F 1/00
(52) U.S. Cl. ...................... 366/348; 366/213; 422/270
(58) Field of Search ........................... 137/268; 134/93, 134/34; 422/261, 269, 270; 366/348

(56) References Cited

U.S. PATENT DOCUMENTS

| | | | |
|---|---|---|---|
| 4,118,192 A | * | 10/1978 | Sawai et al. |
| 4,147,767 A | * | 4/1979 | Yapel, Jr. |
| 4,341,475 A | | 7/1982 | Saladin ....................... 366/211 |
| 5,060,151 A | * | 10/1991 | Mikyska et al. |
| 5,118,794 A | | 6/1992 | Grangeorge et al. ........ 530/363 |
| 5,250,662 A | * | 10/1993 | Chang |
| 5,558,437 A | | 9/1996 | Rode .......................... 366/208 |
| 5,770,028 A | * | 6/1998 | Maley et al. |
| 6,022,954 A | | 2/2000 | Dernis et al. ............... 530/364 |

FOREIGN PATENT DOCUMENTS

| | | |
|---|---|---|
| EP | 0 341 103 A1 | 11/1989 |
| EP | 0 402 205 A1 | 12/1990 |
| EP | 0 875 249 A1 | 11/1998 |
| FR | 2 617 826 | 1/1989 |

OTHER PUBLICATIONS

European Patent Office Search Report dated Dec. 20, 2001.

* cited by examiner

Primary Examiner—Charles E. Cooley
Assistant Examiner—David Sorkin
(74) Attorney, Agent, or Firm—Finnegan, Henderson, Farabow, Garrett and Dunner, L.L.P.

(57) ABSTRACT

The invention proposes a process and an arrangement for dissolving albumin flakes in a liquid which is filled into a container.

In the process according to the invention, it is intended that the flakes are moved relative to the liquid. The arrangement for carrying out the process has a constructional embodiment which permits a number of containers (6) to be treated simultaneously by the process according to the invention, the arrangement having one or more motors (10) for driving the construction elements (3, 4, 7, 8, 9), which move the containers (6) in a rotary or translational motion during the treatment.

6 Claims, 1 Drawing Sheet

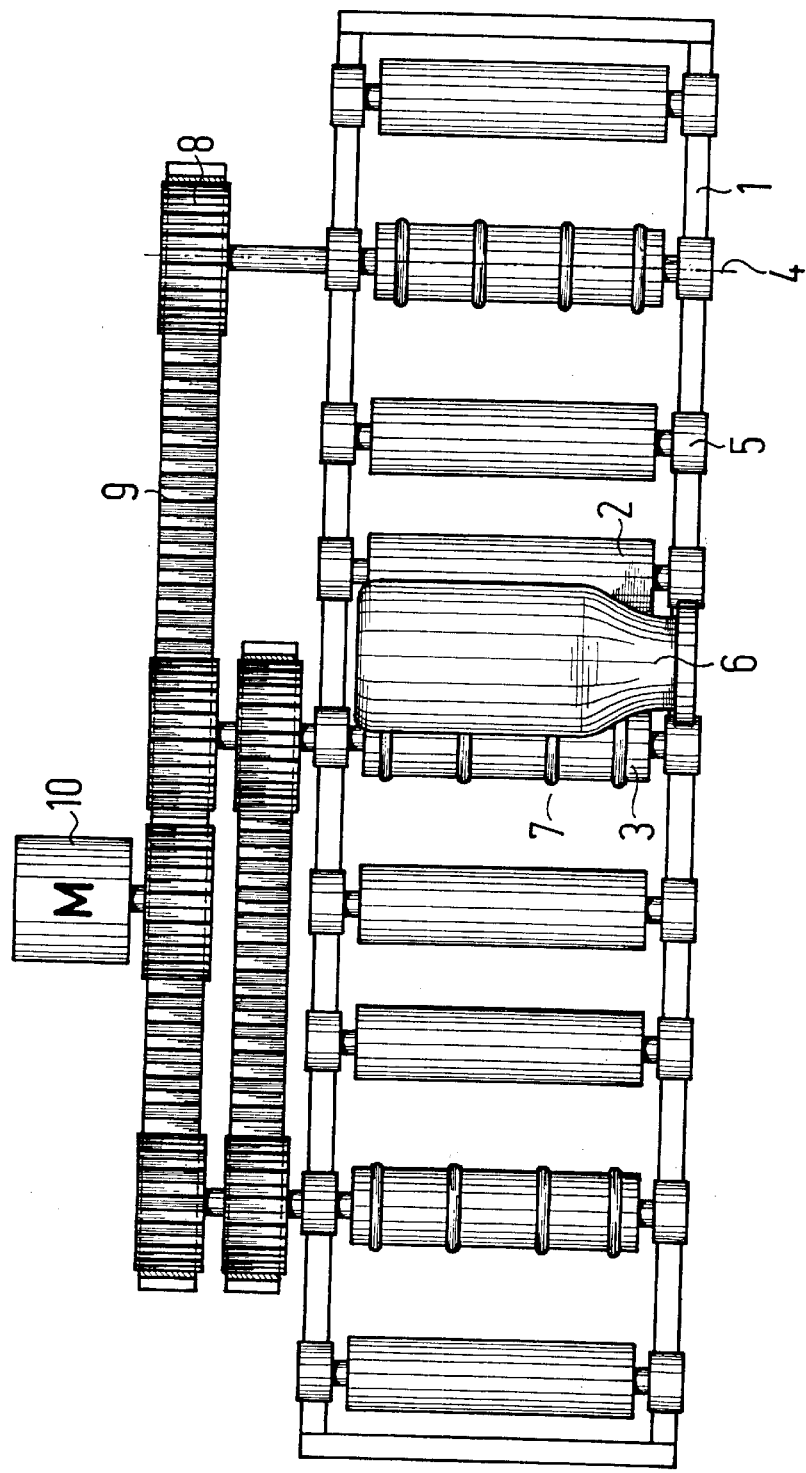

PROCESS FOR DISSOLVING ALBUMIN FLAKES IN A LIQUID AND ARRANGEMENT FOR CARRYING OUT THE PROCESS

The invention relates to a process for dissolving albumin flakes in a liquid and an arrangement for carrying out the process.

In the pasteurized final filling of human albumin, flake formation is often observed. These flake-containing preparations are not marketable and are therefore sorted out in the visual final check of manufacture. The containers at fault, in particular bottles, are opened manually and the contents are emptied into a collecting container. The albumin solution is then filtered to remove flakes. The filtrate is filled into bottles again as in the above manufacturing process and sealed, pasteurized and visually checked. By far the major part of the worked-up albumin solution is free of flakes and can be further processed in the packing line. The working-up of flake goods is personnel-intensive, causes additional costs due to the loss of valuable material and the consumption of primary packaging materials and aids, and increases the amount of waste obtained in the form of used primary packaging materials, filters and wash solutions. In the visual check, flake material assessed as false-negative is the subject of complaints by the customer, leads to returns and can moreover adversely affect the company's image on the market.

It is the object of the present invention to indicate a simple, highly effective process for dissolving albumin flakes in a liquid and an arrangement of constructionally simple design for carrying out the process.

The invention proposes a process for dissolving albumin flakes in a liquid which is filled into a container in such a way that the flakes and the liquid are moved relative to one another.

Within the meaning of the invention, the crucial factor for the kinetics of the dissolution of the flakes in the liquid is the movement of the flakes relative to the bulk of the liquid. In liquids which are filled into bottles, a high relative velocity is in particular guaranteed by rotation of the bottles around their longitudinal axis at a high speed of rotation. On account of the inertia, the velocity difference is the greatest shortly after the beginning of the rotation and directly after the braking of the bottles. The greatest prospects of success for the dissolution of albumin flakes thus consist in the rapid acceleration of the bottles to high speeds of rotation and subsequent rapid braking.

Preferably, the containers are rotated in a horizontal position, as by this means wetting of the entire inner surface, including the stopper, sealing cap or the like is guaranteed.

The repeated acceleration of the bottles can be carried out in the same direction of rotation or alternatively in the opposite direction of rotation, preferably in the opposite direction of rotation.

The invention is not restricted to rotation of the containers or bottles, but the dissolution of the albumin flakes can be carried out by exclusively translational movement with acceleration and braking phases, optionally by a translational movement in opposite directions.

The arrangement for carrying out the process according to the invention has at least the following features:
  a constructional embodiment which permits a number of containers to be treated simultaneously by the process according to the invention,
  one or more motors for driving the construction elements, which move the containers in a rotary or translational motion during the treatment.

It is in particular intended thereby that the containers are of rotationally symmetrical form, in particular bottles.

According to a particular embodiment of the arrangement according to the invention, it is intended that a number of treatment positions are coupled to a multi-positional unit. The treatment positions are preferably arranged next to one another in a plane. The support elements of the treatment positions are to be chosen in their length and in their separation such that the containers can be contained securely and preferably in the lying position between support elements which are in each case adjacent. The supports for the containers to be treated are of rotationally symmetrical design, preferably rollers, cylinders or collars. The ends of the axes of the support elements are contained in suitable bearings, e.g. roller or slide bearings. The treatment sites are composed of driven and loose rollers. To carry out the process according to the invention, the containers lie on one driven and one loosely supported roller in each case. According to a preferred embodiment, it is proposed to choose the division of the treatment unit and the arrangement of the driven and the loose rollers such that two containers can be set in rotation by one driven roller in each case. The composition of the driven rollers is chosen in such a way that an adequate coefficient of friction to drive the containers by means of the rollers results.

This is effected by the construction of the driven rollers from a suitable material or by coating of the rollers with a suitable material or by the application of suitable elements, for example O-rings or circular cord rings of a suitable material, preferably of an elastomer. The coupling of a number of driven rollers with one another and with the drive motor is effected by means of a suitable frictional connection, for example by means of connecting elements such as gears, chains or drive belts, preferably via toothed belts. The drive motor used is an electric motor, preferably with a switchable sense of rotation and with a controllable speed of rotation. The switching-on time, direction of rotation and speed of rotation of the motor are advantageously controlled by means of an automatically operating control unit.

The apparatus according to the invention is not restricted to a design having six treatment sites.

It is also intended for the arrangement of a number of partial treatment units over one another, next to one another or behind one another.

It is also intended for the arrangement of a number of single-site or two-site treatment units each having a separate drive motor.

It is also intended for the combination of the treatment units with automatically operating feeding and removal stations.

It is also intended for the combination of a treatment unit with an apparatus for the simultaneous further transport of the containers.

Further features of the invention are shown in the subclaims, the description of the figures and the FIGURE itself, it being noted that all individual features and all combinations of individual features are essential to the invention.

In the single FIGURE, one embodiment of the invention is shown by means of a schematic representation, without being restricted thereto.

The FIGURE shows an arrangement for dissolving albumin flakes in a liquid which is filled into bottles. This arrangement is shown in a plan view.

A frame 1 contains a total of nine loose rollers 2 and driven rollers 3, which are arranged parallel to one another and in a plane. The axes 4 of the rollers 2 and 3 are carried in roller bearings 5 on both sides of the roller ends. The roller bearings 5 are fixed in corresponding recesses in the frame 1. The length of the rollers 2 and 3 is chosen such that the bottles 6 to be treated can be contained lying parallel to the rollers 2 and 3 of the arrangement in a longitudinal direction.

The driven rollers 3 of the arrangement are each provided with four O-rings 7 of an elastomer material, which are fixed to the driven rollers by corresponding recesses in the driven rollers 3. Owing to the increased coefficient of friction of the O-rings 7, a transmission of the rotary motion of the driven rollers 3 to the bottles 6 to be treated is reliably achieved. The organization of the driven rollers 3 and the loose rollers 2 in the arrangement is chosen such that two bottles 6 in each case can be set into rotation by one driven roller 3 in each case. In this case, each bottle 6 lies on one driven roller 3 and one loose roller 2 in each case. The separations of the rollers 2 and 3 are chosen such that the bottles 6 do not bump against one another.

The axis 4 of one of the externally driven rollers 3 is provided on the rear side of the arrangement with a further toothed disk 8 and is connected to this in a rotationally fixed manner. This toothed disk 8 is connected via a toothed belt 9 with a toothed disk 8 which is frictionally connected to the drive shaft of an electric motor 10. The drive motor 10 is constructed with a switchable direction of rotation and a controllable speed of rotation. The control of the motor 10 with respect to its switching-on time, direction of rotation and speed of rotation is effected by means of an appropriate control unit. By this means, automation of the acceleration and braking of the bottle, and of the change in direction of rotation to optimize the dissolution of the flakes is made possible.

The speed of rotation of the bottles is preferably 200 per minute to approximately 560 per minute, the speed of rotation being upwardly limited start of foam formation.

The process is suitable for the customary bottle sizes in the range 50–1000 ml. In the case of larger and smaller formats, the device must appropriately adjusted.

What is claimed is:

1. A method of dissolving albumin flakes which have formed in a pasteurized solution of human albumin after filling the solution into a container and sealing the container, comprising:

creating movement of the flakes relative to the bulk of the liquid by moving the container and repeatedly alternating acceleration and deceleration of the container.

2. The method as claimed in claim 1, wherein the container is moved in rotary fashion.

3. The method as claimed in claim 2, wherein the container is accelerated to speed between 200 to 560 revolutions per minute, and braked abruptly.

4. The method as claimed in claim 1, wherein the container is moved in opposite directions.

5. The method as claimed in claim 1, wherein the container is moved horizontally.

6. The method as claimed in claim 1, wherein the creating movement of the flakes includes creating movement of flakes attached to an inside of the sealed container.

* * * * *